US006667277B2

(12) United States Patent
Hartmann et al.

(10) Patent No.: US 6,667,277 B2
(45) Date of Patent: Dec. 23, 2003

(54) WATER DISPERSIBLE STARCH BASED PHYSICAL FORM MODIFICATION OF AGRICULTURAL AGENTS

(75) Inventors: Frank D. J. Hartmann, Wilmington, DE (US); James L. Eden, East Millstone, NJ (US); Daniel B. Solarek, Hillsborough, NJ (US); Johan C. G. Rommens, Kortenberg (BE); Mahroussa I. Auda, Sint Denijs Westram (BE)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 15 days.

(21) Appl. No.: 09/938,376

(22) Filed: Aug. 24, 2001

(65) Prior Publication Data

US 2003/0109384 A1 Jun. 12, 2003

(51) Int. Cl.$^7$ ........................ A01N 25/04; A01N 25/08; A01N 57/02

(52) U.S. Cl. ....................... 504/206; 504/360; 504/362; 504/367; 514/407; 514/778; 514/937; 514/950; 514/970

(58) Field of Search ................................ 504/206, 360, 504/362, 367; 514/407, 937, 950, 970, 778

(56) References Cited

U.S. PATENT DOCUMENTS

| | | | | |
|---|---|---|---|---|
| 2,661,349 A | | 12/1953 | Caldwell et al. | 260/224 |
| 3,137,592 A | | 6/1964 | Protzman et al. | 127/32 |
| 3,637,656 A | | 1/1972 | Germino et al. | 260/233.3 R |
| 4,277,364 A | | 7/1981 | Shasha et al. | 252/316 |
| 4,280,851 A | | 7/1981 | Pitchon et al. | 127/33 |
| 5,321,132 A | | 6/1994 | Billmers et al. | 536/48 |
| 5,571,552 A | | 11/1996 | Kasica et al. | 426/573 |
| 5,628,934 A | | 5/1997 | Ohno et al. | 252/586 |
| 6,001,382 A | * | 12/1999 | Levy | 424/405 |
| 6,117,819 A | * | 9/2000 | Priesnitz et al. | 504/206 |
| 6,228,807 B1 | | 5/2001 | Kuchikata et al. | 504/206 |
| 6,358,520 B1 | * | 3/2002 | Lo et al. | 424/408 |
| 2002/0055436 A1 | | 5/2002 | Krause et al. | 504/118 |

FOREIGN PATENT DOCUMENTS

| | | |
|---|---|---|
| EP | 0 352 010 | 1/1990 |
| EP | 0 565 354 | 10/1993 |
| EP | 0 699 389 | 3/1996 |
| JP | 56 072902 | 6/1981 |
| JP | 05 294802 | 11/1993 |
| JP | 06 056603 | 3/1994 |
| JP | 06 298604 | 10/1994 |
| JP | 07 233015 | 9/1995 |
| JP | 08 099804 | 4/1996 |
| WO | WO 89/12449 | 12/1989 |
| WO | WO 95/10184 | 4/1995 |

OTHER PUBLICATIONS

"Starch: Chemistry and Technology", Edited by Roy L. Whistler et al., Second Edition, 1984, Chapter X, pp. 311–388.

"The Chemistry of The Carbohydrates", William Pigman et al., 1948, Chapter XIV: 'The Starches and Starch Substances', pp. 561, 564.

* cited by examiner

*Primary Examiner*—S. Mark Clardy
(74) *Attorney, Agent, or Firm*—Karen G. Kaiser

(57) ABSTRACT

A stable, solid product of selected starches, active agricultural agents and optionally surfactants and or adjuvants which is readily dispersible in aqueous medium and compatible when dispersed.

48 Claims, No Drawings

WATER DISPERSIBLE STARCH BASED PHYSICAL FORM MODIFICATION OF AGRICULTURAL AGENTS

FIELD OF THE INVENTION

This invention relates to water dispersible, stable, solid products or formulations of selected starches, active agricultural agents, and surfactants and/or adjuvants. These solid products are readily water soluble or dispersible. Furthermore, these products have a starch matrix or carrier structure which changes the physical form of the product, makes it compatible when dispersed, allows for a high loading of active material and permits use of a broad range of surfactants, adjuvants and other ingredients. Furthermore and surprisingly, it has been found that such starch containing agrochemical products can exhibit increased biological efficacy of the active material.

Various formulations of agricultural active ingredients have been developed to satisfy the needs for agricultural crop protection and other related areas. Oftentimes these products have been in the form of liquid formulations.

Recently, in crop protection formulation technology there has been a desire to move away from liquid formulations to solid products such as dry granules or powders. Such solid products would reduce the use of solvents, be more environmentally friendly and reduce transportation costs. However, the ability to provide solid products using a combination of active ingredients such as glyphosate, and surfactants such as polyoxyethylene sorbitan esters, e.g. Tween 20, has been difficult because such materials are not compatible and are not easy to process or work with. Although much effort has been made to develop solid agricultural products, most of the useful solid, starch based products exhibit extended or delayed release characteristics.

U.S. Pat. No. 6,228,807 issued on May 8, 2001 to M. Kuchikata et al, discloses dry, water-soluble herbicidal compositions of glyphosate with selected surfactants. While such compositions are water dispersible, it is difficult to form compatible solutions since many surfactants are not compatible with glyphosate in concentrated form.

Despite the various disclosures of active agricultural products, including the recent '807 patent noted above, and solid products showing extended release properties, there is still the need for solid agricultural type products which are water dispersible, compatible when dispersed and exhibit quick release characteristics.

Accordingly, what is desired for use in agricultural applications, is a stable, solid product which has quick release properties, provides high load of active materials and can combine multiple components into a compatible system.

SUMMARY OF THE INVENTION

Now it has been found that stable, water dispersible solid products of agricultural active agents are provided when combined with selected starches and optionally surfactants and/or adjuvants.

More particularly, this invention is directed to a stable, dry solid formulation which is water dispersible and provides a rapid, compatible, homogeneous dispersion and comprises:

a) a chemically modified starch, b) a biologically active agricultural material, and optionally c) a surfactant and/or adjuvant.

This invention further involves agrochemical formulations containing combinations of two or more active materials.

DETAILED DESCRIPTION OF THE INVENTION

This invention involves stable, water dispersible solid products of selected starches, agricultural active agents, and surfactants and/or adjuvants. These dry solid products or formulations are rapidly dispersed in aqueous medium, compatible when dispersed and provide quick release of the bioactive agent. These formulations also provide a high loading of the active ingredient and have been found especially useful in agricultural crop protection. Furthermore, the solid product of this invention has a starch matrix which allows for the use of one or more different active materials and the use of a wide variety of surfactants, adjuvants and other ingredients while still providing a compatible dispersion and high load capacity.

Stable, solid products are those where there is no bleeding or separation of individual components. Generally a product is considered stable when this condition exists for at least six months.

Dispersible, solid products are those which are functionally uniform or homogeneous when dispersed. The dispersed or water solubilized product may be in the form of a solution, emulsion or suspension.

Compatible solutions are those where the individual components remain homogeneous in the final aqueous solution. Compatible emulsions in water are those that remain stable, do not coalesce, phase out or separate, flocculate, aggregate or produce sediment. For compatible suspensions in water, the solids remain homogeneously suspended in the end use dispersion, i.e. they do not drop out. The compatible solutions or dispersions provide relatively or functionally uniform distributions of the components in the end use liquid. Compositions are typically considered compatible when these conditions exist for at least 4 hours and more particularly 24 hours or more.

Rapidly or readily dispersible is defined as a mixture with cold water and minimal agitation that gives a dispersion in less then 10 minutes, more particularly less then 3 minutes.

Solid products are those such as the type having a particulate form or structure and having a wide range of sizes and shapes, such as powders, granules (dust free powders), flakes, chips, sheets, tablets, pellets, agglomerates, etc.

The solid product or formulation of this invention will comprise either the combination of starch, active material and surfactant and/or adjuvant; starch and active material; or starch and surfactant and/or adjuvant. Any of the above formulations may also include optional additive ingredients.

The active ingredients used in the system or formulations of this invention include a broad range of materials and this includes active ingredients some of which don't form free standing powders on their own. Some of the useful active materials may be liquid while others may be solids with low or high melting points. Particularly useful active ingredients for this invention are liquids at room temperature or low melting (e.g. <80° C.) materials and high melting (e.g. >80° C.) crystalline materials.

The agricultural active agents which are used in the formulations of this invention can be any one or more of a wide range of water dispersible agrochemically active materials. Description of the actives as water dispersible means that they are water soluble or can be suspended or emulsified in water. More particularly, it may be one or more herbicides, pesticides, for example insecticides, fungicides, acaricides, nematocides, miticides, rodenticides, bactericides, mollusicides and bird repellants, and/or plant growth regulators. Especially useful active materials are herbicides, insecticides and fungicides. Usually, the active material will be a water insoluble or immiscible material, although granules can be made including water soluble active materials. Specific examples of active materials include:

Herbicides such as 6-chloro-N-ethyl-N-(1-methylethyl)-1,3,5-triazine-2,4-diamine (common name atrazine); N,N'-bis(1-methylethyl)-6-(methylthio)-1,3,5-triazine-2,4-diamine (common name prometryn); substituted ureas such as diuron or N'-(3,4-dichlorophenyl)-N,N-dimethylurea); sulfonyl ureas such as metsulfuron-methyl{2-[[[[(4-methoxy-6-methyl-1,3,5-triazin-2-yl) amino]carbonyl] amino]sulfonyl]benzoate}; triasulfuron {2-(2-chloroethoxy)-N-[[(4-methoxy-6-methyl-1,3,5-triazin-2-yl) amino]carbonyl]benzenesulfonamide}; tribenuron-methyl {methyl 2-[[[[(4-methoxy-6-methyl-1,3,5-triazin-2yl)-methylamino]carbonyl]amino]sulfonyl]benzoate} and chlorsulfuron {2-chloro-N-[[(4-methoxy-6-methyl-1,3,5-triazin-2-yl)amino]carbonyl] benzenesulfonamide}; bis-carbamates such as phenmedipham or {3-[(methoxycarbonyl)amino] phenyl (3-methylphenyl) carbamate}, aryloxyalkanoic acids like [(3,5,6-trichloro-2 pyridinyl)oxy] acetic acid (commonly known as triclopyr) and its salts or esters like triclopyr-triethanolammonium, triclopyr-butotyl, (2,4 dichlorophenoxy) acetic acid (commonly known as 2,4-D) and its salts or esters like 2,4-D butyl, 2,4-D-dimethylammonium, 2,4-D-diolamine, 2,4-D-2-ethylhexyl, 2,4-D-isooctyl, 2,4-D-isopropyl, [(4-amino-3, 5-dichloro-6-fluoro-2-pyridinyl)oxy] acetic acid (commonly known as fluoropyr) and its esters like furoxypyr-meptyl and fluroxypyr-2-butoxy-1-methylethyl, 2-(4-aryloxyphenoxy) propionic acids like butyl (±)-2-[[5-(trifluoromethyl) 2 pyridinyl]oxy]phenoxy]-propanoate (commonly known as fluazifop-butyl), (±)-2-[4-[[3-chloro-5-(trifluoromethyl)-2-pyridinyl]oxy]phenoxy]propanoic acid (commonly known as haloxyfop) and its esters haloxyfop-etotyl, haloxyfop-methyl, haloxyfop-P-methyl, butyl (R)-2-[4-(4-cyano-2-fluorophenoxy) phenoxy]propionate (commonly known as cyhalofop-butyl), cyclohexanedione oximes like (±)-(EZ)-2-(1-ethoxyiminobutyl)-5-[2-(ethylthio)propyl]-3-hydroxycylohex-2-enone (commonly known as sethoxydim). Additional useful herbicides include alpha-chloro-2',6'-diethyl-N-methoxymethyl acetanilide (commonly known as alachlor), N-butoxymethyl-alpha-chloro-2',6'-diethylacetanilide (commonly known as butachlor), 2'-methyl-6'-ethyl-N-(1-methoxy-prop-2-yl)-2-chloroacetanilide (commonly known as metolachlor), isobutyl ester of (2,4-dichlorophenoxy) acetic acid, 2-chloro-N-(ethoxymethyl)-6'-ethyl-o-acetotoluidide (commonly known as acetochlor), 1-(1-cyclohexen-1-yl)-3-(2-fluorophenyl)-1-methyl urea, S-2,3,3-trichloro-allyl-diisopropyl thiocarbamate (commonly known as triallate), and alpha, alpha, alpha-trifluoro-2,6-dinitro-N,N-dipropyl-p-toluidine (commonly known as trifluralin).

Fungicides such as thiocarbamates, particularly alkylenebis(dithiocarbamate)s, for example maneb or {[1, 2-ethanediylbis-[carbamodithiato] (2-)] manganese} and mancozeb or {[[1,2-ethanediyl-bis[carbamodithiato]](2-)] manganese mixture with [[1,2-ethanediylbis [carbamodithiato]] (2-)]zinc}; strobilurins such as azoxystrobin (methyl (E)-2-[[6-(2-cyanophenoxy)-4-pyrimidinyl]oxy]-a-(methoxymethylene) benzeneacetate} and kresoxim-methyl {(E)-a-(methoxyimino)-2-[(2-methylphenoxy)methyl]benzylacetic acid methyl ester}; dicarboximides such as iprodione {3-(3,5-dichlorophenyl)-N-isopropyl-2,4-dioxoimidazoline-1-carboxamide}; azoles such as propiconazole or {1-[2-(2,4-dichloro-phenyl)-4-propyl-1,3-dioxolan-2-yl-methyl-1H-1,2,4-triazole and tebuconazole or {(RS)-1-p-chlorophenyl-4,4-dimethyl-3-(1H-1,2,4-triazole-1-ylmethyl)-pentan-3-ol}; halophthalonitriles such as chlorothalonil pr {2,4,5,6-tetrachloro-1,3-dicyanobenzene}; and irorganic fungicides such as copper hydroxide or Cu(OH)2.

Insecticides including benzoyl ureas such as diflubenzuron or N-[[(4-chlorophenyl)amino]carbonyl]-2,6-difluorobenzamide; carbamates including solid and liquid forms such as carbaryl or 1-naphthyl methyl carbamate, aldicarb, methomyl, carbofuran, bendiocarb, oxamyl, thiodicarb, trimethylcarb; organophosphates e.g. malathion, parathion, demeton, dimethoate, chlorpyrifas, diazinon, azinphosmethyl and phosmet; compounds which break down an insect's digestive tract tissue including fluorine compounds (cryolite), zinc and mercury; nicotine; rotenone; neem oil or azadiractin; natural or synthetic pyrethrins, permethrin, lamda-cyhalothrin, cypermethrin, petroleum oils; and microbials e.g. bascillus thuringiensis and entomopathic viruses such as the bacculo virus.

Acaricides such as clofentezine or 3,6-bis(2-chlorophenyl)-1,2,4,5-tetrazine.

Among water soluble active materials, non-selective herbicides, particularly N-(phosphonomethyl) glycine type herbicides such as glyphosate and sulphosate, respectively the iso-propylamino and trimethylsulphonium salts of N-phosphonylmethyl glycine, and other salts such as ammonium, sodium and potassium; and phosphinyl amino acids such as glufosinate or 2-amino-4-(hydroxymethylphosphinyl)butanoic acid, particularly as the ammonium salt. Such water soluble actives can be used as the sole active in water dispersible granules or in combinations thereof, but can also be used in combination with water insoluble or immiscible actives in multi-active formulations.

The agrochemical formulation of this invention can include one or more surfactants and/or adjuvants and other additive ingredients. Surfactants have surface active properties and help to increase the dispersibility of the active material and/or can also act as an emulsifier, solubilizer, wetting agent or suspending agent. Adjuvants are materials that help to increase the biological efficacy of the active material and include surfactants, oils such as mineral oils, vegetable oils and alkyl esters of fatty acids, and combinations thereof. Other additive ingredients and materials can be used to provide a variety of functional attributes to the formulation and include materials such as buffering agents, rheological modifiers, antifoam/defoamers, drift/mist control agents, viscosifiers, emulsifiers, dispersants, suspending agents, solvents and fillers. One or more of such surfactants, adjuvants and other additves may be used and they are not limited by physical form such as liquid, paste or wax; or by being water soluble (i.e. from fully water soluble to water insoluble) or water dispersible (e.g. forming aqueous solutions, dispersions or emulsions). The surfactant or adjuvant may help increase the biological efficacy of the active material. The particular surfactant and/or adjuvants that are used in the formulation will depend on the active material and its properties.

The surfactant used in the formulation may be non-ionic, cationic, anionic, amphoteric or a blend or combination thereof. Exemplary non-ionic surfactants include alcohol alkoxylates, e.g. ethoxylates, particularly C8 to C18 alcohols which can be linear, branched or linear/branched mixtures;

alkylamine alkoxylates, e.g. ethoxylates and particularly C8 to C18 alkylamines; sorbitol and sorbitan fatty acid esters, particularly C8 to C18 fatty acids esters and their ethoxylated derivatives; and chemically modified low molecular weight polysaccharides, particularly C6 to C14 alkyl polysaccharides such as alkylpoly-glycosides. Other non-ionics include polyoxyethylene-polyoxypropylene block copolymers, glycerol esters, glycol esters, alkoxylated and non-alkoxylated sorbitan esters, sucrose esters, sucrose glycerides, polyoxyalkylene alkylaryl ethers, polyoxyalkylene alkyl esters and fatty acid ethoxylates.

Cationic surfactants that are useful include primary, secondary and tertiary alkylamines, tertiary polyoxyalkylene alkylamines, polyoxyalkylene and non-polyoxyalkylene alkylamine oxides, tertiary polyoxyalkylene alklyetheramines, polyoxyalkylene alkyletheramine oxides, and tetra alkylammonium halides.

Useful anionic surfactants include alkyl sulfates and phosphates, olein sulfonates, alkylaryl sulfonates, polyoxyalkylene alkylether sulfates and phosphates, sulfosuccinate derivatives, sulfosuccinates, sarcosinates, taurates, sulfates and sulfonates of oils.

Useful amphoteric surfactants include N-alkylbetaines, alkyl amidobetaines and imidazoline derivatives.

The selected starch component which can be used in the solid products or formulations of this invention are chemically modified starches and more particularly are starch esters and starch ethers. The starch esters and starch ethers may contain nonionic or ionic substrate groups such as cationic, e.g. tertiary amine and quaternary ammonium groups, or anionic groups, and may be crosslinked. Modified starches of these types are described in "Starch: Chemistry and Technology", edited by R. L. Whistler et al, Chapter X, 1984. Preferred modified starches are those containing an ester or ether group. The base starch may be any starch, native or converted, and includes those derived from any plant source such as maize, tapioca, potato, wheat, rice, sago, sorghum, waxy maize, waxy potato and high amylose starch, i.e. starch having at least 40% by weight of amylose content. Also included are the conversion products derived from any of the former bases including, for example, dextrin prepared by hydrolytic action of acid and/or heat; oxidized starches prepared by treatment with oxidants such as sodium hypochlorite or hydrogen peroxide; and fluidity or thin boiling starches prepared by enzyme conversion or mild acid hydrolysis.

Modified starch esters include starch acetate, starch propionate, starch butyrate, starch hexanoate etc. as well as the half-esters of dicarboxylic acids, particularly the alkenylsuccinic acids. Starch ethers include the hydroxyalkyl ethers such as hydroxyethyl and hydroxypropyl starch. The starch esters and ethers used in this invention may be prepared by processes known in the art such as disclosed in "Starch: Chemistry and Technology", noted above.

The preparation of starch esters typically involves reacting starch with organic acid anhydrides such as acetic anhydride in either aqueous or non-aqueous systems, e.g. anhydrous pyridine. A review of such preparations may be found in "Starch: Chemistry and Technology", edited by R. L. Whistler et al, Chapter X, 1984, as well as in U.S. Pat. No. 2,661,349 issued to C. Caldwell et al on Dec. 1, 1953 and U.S. Pat. No. 5,321,132 issued to R. Billmers et al on Jun. 14, 1994. The '349 and '132 patents are hereby incorporated herein by reference.

One modification of starch that is especially useful in this invention is a starch ester prepared from an organic acid anhydride having a hydrophobic group such as octenyl or dodecenyl succinic anhydride. More particularly, the hydrophobic group is a hydrocarbon group such as alkyl, alkenyl, aralkyl or aralkenyl having 2 to 22 carbons, preferably 5 to 18 and more preferably 8 to 12 carbons. Generally the starch will be treated with up to 60%, more particularly 1 to 60% and preferably 5 to 20% by weight of the anhydride, based on the weight of starch.

Another modification of starch that is especially useful in this invention is the etherification with alkylene oxides, particularly those containing 2 to 6, preferably 2 to 4 carbon atoms. Ethylene oxide, propylene oxide and butylene oxide are exemplary compounds that are useful in etherifying the starting starch materials. Although varying amounts of such reagent compounds may be used, generally up to 25%, more particularly 1 to 25% and preferably 1 to 10% by weight, based on the weight of starch, will be used.

The modified starches as used herein may be degraded or converted to achieve certain viscosity characteristics and allow for better interaction with components. The modified starches may also be pregelatinized or crosslinked. The degraded starches can vary from 15 to 90 WF (i.e. water fluidity). In addition, dextrins and/or multi-dextrins of <10 DE (dextrose equivalent) can be used. Degradation can be carried out using conventional processes such as oxidative hydrolysis including treatment with hydrogen peroxide, enzyme hydrolysis or acid hydrolysis. Such degradation can be performed either before or after modification is made to the starch.

The important feature of this invention is being able to provide an agrochemical formulation or surfactant and/or adjuvant system in the modified physical form of a stable, solid such as a free-flowing powder. This can be accomplished when using either a water soluble active material or a water insoluble active material, i.e. emulsifiable or suspendable oily or non-water soluble active materials. This can include mixtures of two or more different active materials such as two or more water soluble or two or more water insoluble active materials or combinations thereof. The active materials do not have to be of the same physical form, e.g. liquid or solid. The ability to do this is provided by use of the selected modified starches as defined herein. The starch provides a matrix for the system and changes the physical form thereby allowing for the use of different surfactants and adjuvants including those in aqueous solutions, oils, waxes, emulsions, etc. Additionally, while previously it has been difficult to incorporate liquid surfactants or adjuvants into the formation of solid products such as powders, the use of starch as described herein, has allowed for the use of such liquids as well as solid surfactants or adjuvants.

The dry solid can be made by dissolving or dispersing the active material, surfactant and/or adjuvant in a starch cook by either mixing the components with raw starch then cooking, e.g. jet cooking, or by mixing the components into cooked starch. Raw starch is generally refined and recovered from plant tissue as microscopic semi-crystalline particles termed granules. These raw granules must be disrupted or gelatinized, usually by heating in a water suspension or slurry, to produce a colloidal dispersion, solution or starch cook. Gelatinization in water or other solvent, is required to allow the starch cook to provide film or matrix forming properties after drying. A wide range of cooking processes are generally suitable, such as, atmospheric pressure batch cooking, elevated pressure batch cooking (autoclaving), steam injection cooking (jet cooking) at either theoretical or excess steam addition ratios, or non diluting heat transfer methods. See "Chemistry of the Carbohydrates", by W. W. Pigman and R. M. Goepp, Academic Press, 1948, p. 561f. Pre-gelatinized starches that do not require the cooking step before adding the starch to the surfactant and/or adjuvant can also be used. The pre-gelatinized starches are readily available and can be produced by many methods such as disclosed in U.S. Pat. No. 4,280,851 issued to Pitchon et al. in July, 1981; U.S. Pat. No. 5,571,552 issued to Kasica et al. in November, 1996; U.S. Pat. No. 3,086,890 issued to Sarko et al. in April, 1963; U.S. Pat. No. 3,637,656 issued to Germino et al. in January, 1972 and U.S. Pat. No. 3,137,592 issued to Protzman et al. in June, 1964. All of these patents are hereby incorporated herein by reference. These mixtures are then dried into a solid such as powder by spray drying or using other drying techniques such as drum drying, extrusion, belt drying or freeze drying.

In a similar manner, the solid product can be made by dissolving or dispersing a) the active material, or b) the surfactant and/or adjuvant in a starch cook by either mixing the components with raw starch and cooking or by mixing the components with cooked starch or pre-gelatinized starch. These mixtures are then dried into solids such as powders using drying techniques such as spray drying, drum drying, extrusion, belt drying or freeze drying. Also, similar products can be prepared with the addition of other additive materials to the components of the above described systems.

While the form of the solid pieces resulting from the process of preparation may be in various sizes and shapes, one particularly useful form are granules which are considered dustless or have particles with sizes of between about 250 to 800 microns. An especially useful process for drying the aqueous feedstock and obtaining dust free granules of useful diameters in one process step is disclosed in U.S. Pat. No. 5,628,937 issued to Oliver et al., which is hereby incorporated by reference. Additional processing such as agglomeration, compact granulation or extrusion can be used, if desired, to attain a more specific particle size range.

The solid formulations of this invention are characterized by high loading of the active ingredient and rapid homogeneous dispersibility in aqueous medium. The amount of starch in the system can vary but generally will be less than about 85% by weight. There should be enough starch to make stable solid such as a free flowing powder.

The amount of active material and other components in the load which make up the formulation can vary. Load is defined as the total amount of active material, surfactant, adjuvant and optional other additive ingredients in the formulation. The formulation will comprise, on a dry basis, from about 15 to 85% by weight of load and from about 15 to 85% by weight of starch, more particularly from about 20 to 80% by weight of load and from about 20 to 80% by weight of starch, and most particularly from about 30 to 70% by weight of load and about 30 to 70% by weight of starch. The percent (%) load is the anhydrous (dry) weight of the load divided by the anhydrous (dry) weight of the total formulation (i.e. load plus starch)×100. The load may be comprised of from about 0 to 100% by weight of active, from about 0 to 100% by weight of surfactant and/or adjuvant, and from about 0 to 90% of other additive ingredients with the proviso that there be at least 10% by weight of active and/or surfactant and/or adjuvant with other additive ingredients. The load may also be completely comprised of active material or surfactant/adjuvant when only one of such components is present.

Any load component which is a non-water soluble liquid or meltable solid usually must be emulsified. The hydrophobically modified starches provide very useful emulsifying properties. Small particle emulsions allow higher loading of emulsified materials and remain as stable products when dried. Furthermore, smaller particle size may give increased efficacy of the active ingredients or improve the agricultural activity of the other ingredients.

The formulation of this invention as described herein may comprise more than one of the components, i.e. one or more active materials, surfactant/adjuvants and starch materials and combinations thereof. The different individual materials do not have to be of the same physical form (e.g. liquid or solid). The ability to be able to do this is due to the selected starch component which forms a matrix and helps provide a stable, compatible system even when using materials or components with different physical forms.

It is further noted that while the solid formulated product containing an active material, and/or surfactant/adjuvant in a starch matrix is a desired or preferred embodiment of this invention, this is because such solid product can be readily dispersed in water to conveniently, quickly and accurately provide a tank spray mixture for ready use in an agrochemical application. However, the components may be used separately without forming a solid or powder. Thus the individual components, i.e. active material, and/or surfactant/adjuvant can be added or combined separately in water along with the starch to form an aqueous dispersion (e.g. in a spray tank). These materials can be used in agrochemical applications or may have other uses apparent to one skilled in the art. One such application involves the combination of starch and surfactant which can be used as a soil or substrate wetting agent. The varied and different useful applications are derived in part from the starch component, which not only is useful as a matrix or solid carrier for the active material and other components but also helps to increase biological efficacy, i.e. it has adjuvant characteristics.

The aqueous dispersion, as noted above, containing starch and active material along with optional surfactant/adjuvant, can be formed by redispersing the solid product of the components or by adding the components together or separately in water. This aqueous dispersion containing the active material along with starch and optional surfactant/adjuvant has an increased biological efficacy. This makes the dispersion particularly useful as a herbicide, pesticide and plant growth regulator for applications to agricultural crops, vegetation, weeds, plants, insects, pests and soil. Particularly useful in providing biological efficacy are starches combined with glyphosate, such as glyphosate-isopropyl amine (IPA), and strobilurin, such as azoxystrobin, active materials. Especially useful combinations are starches combined with glyphosate-isopropyl amine (IPA) and polyoxyethylene sorbitan ester (Tween 20) and starches combined with azoxystrobin and non-ionic surfactants, (ethoxylated C8 to C18 alcohols).

Besides being used as a redispersed solid or by application from an aqueous dispersion, the starch containing products can also be used as a solid in dry form without dispersing in water. For example, the starch entrapped product can be broadcast onto soils as a powdered particulate or pest bait. Another embodiment of this invention involves a solid product containing a surfactant or adjuvant, particularly a non-oil adjuvant, in a starch matrix.

The water soluble starch containing solid of this invention, is a stable mixture which is compatible and quickly releases the active ingredient and adjuvants once dispersed in the spray or feed tank. These products have been found to provide a high loading of active ingredient and surfactant/adjuvant and also allow for use of a broad range of surfactant chemistries. Furthermore and surprisingly, use of these products result in beneficial properties such as increased biological activity and increased rainfastness.

The invention is further illustrated by the following examples with all parts and percentages given by weight and all temperatures in degrees Celsius, unless otherwise noted.

EXAMPLE 1

Several samples of liquid alkyl (C8–C10) polyglycoside with different starches were prepared by making an aqueous feedstock solution, spray drying the feedstock and recovering the resulting powder.

The starches identified in Table 1 as samples A–F, were slurried in water and jet cooked in a model C-1 steam direct injection continuous cooker (National Starch & Chemical Co.) at about 140° C. The solids of the cooked starches A, B, and D–F were 30% while the solids of starch C was 20%. The polyglycoside amount, as shown in Table 1, was added to the cooled starch of each formula, mixed until uniform and then heated to about 50° C. Water was added, if required, to dilute the feed to a rheology and viscosity suitable for atomization. Samples were processed on a Bowen laboratory scale dryer (GEA Niro, Columbia, Md.) using a rotary wheel atomizer. Dryer inlet temperatures were about 205 to 230° C. and outlet temperatures were about 90 to 120° C.

In all cases the formed products were stable, free flowing and rapidly soluble powders. As further noted in the table below, relatively high loadings of up to 80% of the polyglycoside (APG) were formed into the water soluble, dry powder.

TABLE 1

Formulations spay dried into powder

| Sample | Starch(1) | Ratio starch/polyglycoside |
|---|---|---|
| A | waxy maize, OSA | 50/50 |
| B | waxy maize, OSA/dextrin | 50/50 |
| C | hydroxypropylated waxy maize (lightly degraded) | 50/50 |
| D | 3% OSA modified waxy maize | 32/68 |
| E | 3% OSA modified waxy maize | 20/80 |
| F | 5% OSA modified waxy maize | 20/80 |

(1)OSA—octenyl succinic anhydride

EXAMPLE 2

A tank spray mix solution was made by dissolving sample B from Example 1 in water and adding glyphosate-IPA (isopropyl amine) solution to give a ratio of glyphosate acid (acid equivalent—a.e.) to alkyl polyglycoside of 2 to 1. A control tank mix solution, without starch, was made by dissolving alkyl polyglycoside in water and adding glyphosate-IPA solution to give a ratio of glyphosate acid to alkyl polyglucoside of 2 to 1.

The tank mixes were prepared to deliver by spraying at two application rates as shown in Table 2, i.e. starch containing solutions F2 and F4 and non-starch containing control solutions F1 and F3.

TABLE 2

| | Application Rates | | |
|---|---|---|---|
| Samples | Glyphosate (g a.e./ha) | Glycoside (g/ha) | Starch (g/ha) |
| F1 | 400 | 200 | — |
| F2 | 400 | 200 | 200 |
| F3 | 800 | 400 | — |
| F4 | 800 | 400 | 400 |

These formulations were applied by spraying onto plant weed species Barley and Malva sylvestris and the efficacy determined as % Kill (0% untreated control plants, 100% treated plants are dead) of the target weeds 7, 14 and 21 days after treatment (DAT). The results were compared with control samples F1 and F3 which did not contain the modified starch carrier. The results are shown below in Table 3 and the % fresh weight (amount of remaining plant tissue) was measured 25 DAT (days after treatment) and expressed as a percentage fresh weight compared to the untreated control.

TABLE 3

| | % Kill | | | |
|---|---|---|---|---|
| Samples | 7 DAT | 14 DAT | 21 DAT | % Fresh Weight |
| | | Barley | | |
| F1 | 42.9 | 42.9 | 82.1 | 12.2 |
| F2 | 25 | 39.3 | 85.7 | 11.9 |
| | | Malva sylvestris | | |
| F3 | 14.3 | 25 | 39.3 | 43.7 |
| F4 | 25 | 28.6 | 42.9 | 25.7 |

As shown in Table 3, the combination of starch and glycoside increased the biological efficacy resulting in increased % Kill and reduced % Fresh Weight.

EXAMPLE 3

Samples of starch with different surfactants were formed into dry powders as in Example 1. The successfully formed powders were stable, non-sticky, dry powders that quickly dissolved in water and were compatible when dispersed. The formulations and amounts of starch and surfactant components are given below in Table 4.

TABLE 4

| Starch(1) | Surfactant(2) | Ratio starch/surfactant |
|---|---|---|
| Waxy maize-OSA | Tween 20 | 50/50 |
| " | Atplus MBA 1303 | 50/50 |
| Hydroxypropylated waxy maize (lightly degraded) | Tween 20 | 50/50 |
| Waxy maize-OSA/ dextrin | Altox MBA 13/15 | 50/50 |
| Waxy maize-OSA/ dextrin | Tween 20 | 50/50 |

(1)OSA—octenyl succinic anhydride
(2)Tween 20 - polysorbate 20
Atplus MBA 1303 - C12–C15 monobranched ethoxylated and propoxylated alcohol
Altox MBA 13/15 - C12–C15 monobranched ethoxylated alcohol

EXAMPLE 4

Several sample formulations of glyphosate-IPA (isopropyl amine) salt, with different starches and adjuvant/ surfactants were formed into free flowing powders as follows. The process used consisted of preparing an aqueous feedstock solution, spray drying the feedstock and recovering the resulting powder. In all cases the product was a stable, free flowing, rapidly soluble powder.

Md.) using a rotary wheel atomizer. Dryer inlet temperatures were about 205 to 230° C. and outlet temperatures ere about 90 to 120° C.

The different sample formulations F1–F11 are shown below in Table 6.

TABLE 6

Dry Powder Sample Formulations (w/w %)

| Samples | F1 | F2 | F3 | F4 | F5 | F6 | F7 | F8 | F9 | F10 | F11 |
|---|---|---|---|---|---|---|---|---|---|---|---|
| Glyphosate-IPA | 33.3 | 43.8 | 33.3 | 43.8 | 33.3 | 33.3 | 43.8 | 43.8 | 43.8 | 43.8 | 43.8 |
| Surfactants | | | | | | | | | | | |
| Tween 20 | 16.7 | 16.2 | — | — | — | — | — | 16.2 | 16.2 | — | 16.2 |
| C8–10 poly glycoside | — | — | 16.7 | 16.2 | — | — | 16.2 | — | — | 16.2 | — |
| Atplus MBA 1303 | — | — | — | — | 16.7 | 16.7 | — | — | — | — | — |
| Starches (1) | | | | | | | | | | | |
| A | 50 | — | 50 | — | 50 | — | — | — | — | — | — |
| B | — | 40 | — | 40 | — | 50 | — | — | — | — | — |
| C | — | — | — | — | — | — | 40 | 40 | — | — | — |
| D | — | — | — | — | — | — | — | — | 40 | 40 | — |
| E | — | — | — | — | — | — | — | — | — | — | 40 |

(1) A—hydroxypropylated waxy maize (lightly degraded)
B—waxy maize octenyl succinic anhydride (OSA)
C—6% OSA modified waxy maize
D—5% OSA modified waxy maize
E—cationic crosslinked waxy maize The starches identified in Tables 6 were slurried in water and jet cooked in a model C-1 steam direct injection continuous cooker (National Starch & Chemical Co.) at about 140° C. Solids of the cooked starches as well as other dryng conditions are show below in Table 5. The glyphosate and the adjuvant/surfactant for each formula (identified in Table 6) were added to the cooked starch which was mixed until uniform and then heated to about 50° C. Water was added, if required, to dilute the feed to a rheology and viscosity suitable for atomization.

TABLE 5

| Starch | Product Formulat. | Dryer | % Cook Solids | % Feedstock Solids | Feedstock-Viscosity cps |
|---|---|---|---|---|---|

TABLE 7-continued

| Sample | Starch (1) | Surfact./Adj. | Active | Wt. Ratio star/surf./adj./act. | Dissolution Time (3) |
|---|---|---|---|---|---|
| 9 | D | C8–10 alkyl polyglycoside | (2) | 33/17/50 | 3'30" |

(1) A—Amioca waxy maize, 3% octenyl succinic anhydride (OSA)
B—waxy maize-octenyl succinic anhydride (OSA)
C—3% OSA modified waxy maize
D—waxy maize, OSA, dextrin
E—tapioca dextrin
(2) glyphosate-IPA (isopropyl amine)
(3) ' = minutes
" = seconds

EXAMPLE 6

Several samples containing different starches with glyphosate-IPA (isopropyl amine) active material and Tween 20 adjuvant were prepared as solutions using amounts of active/adjuvant of 2/1 and active/adjuvant/starch of 2/1/1.3. These samples were tested for rainfastness by applying them to target weeds (velvetleaf—Abutilon theophrasti) using amounts of glyphosate-IPA active of 0.54 lb acid equivlaent (a.e.)/acre (600 g. a.e./ha) (low dose) and 0.9 lb a.e./acre (1000 g. a.e./ha) (high dose). The samples were applied by forming solutions and spraying at 21.4 gal/acre (200l/ha). Rainfall was applied 1 hr. after treatment at 3 min./hr. for 1 hour. The results in Table 8 and Table 9 show the effects of rain, expressed as % kill, on the different starch formulations and the resulting fresh weight amount of remaining plant tissue 20 days after treatment (DAT).

TABLE 8

Effect of Rain on Starch formulations applied on Abutilon theophrasti 20 DAT

| | % Kill | | | |
|---|---|---|---|---|
| | Low Dose | | High Dose | |
| Starch | No Rain | Rain | No Rain | Rain |
| None | 60.71 | 32.14 | 96.43 | 42.86 |
| (1) | 75 | 39.29 | 100 | 53.57 |
| (2) | 82.14 | 42.86 | 92.86 | 60.71 |
| Sago | 96.43 | 42.86 | 100 | 53.57 |
| (3) | 75 | 42.86 | 96.43 | 46.43 |

(1) 6% octenyl succinic anhydride (OSA) modified waxy maize
(2) 70WF, 3% OSA modified waxy maize
(3) 75WF, 3% OSA modified corn starch As shown in Table 8, the starch containing spray solutions improved the rainfastness resulting in an increased % Kill at both the low dose and high dose.

TABLE 9

Fresh Weight of Abutilon theophrasti 20 Days After Treatment (DAT)

| | % Fresh Weight | | | |
|---|---|---|---|---|
| | Low Dose | | High Dose | |
| Starch | No Rain | Rain | No Rain | Rain |
| None | 28.29 | 60.62 | 15.23 | 50.9 |
| (1) | 22.1 | 68.58 | 15.51 | 36.1 |
| (2) | 19.76 | 52.07 | 13.57 | 35.82 |
| Sago | 13.99 | 55.83 | 10.7 | 38.99 |
| (3) | 23.89 | 60.17 | 9.97 | 42.29 |

(1) 6% octenyl succinnic anhydride (OSA) modified waxy maize
(2) 70WF, 3% OSA modified waxy maize
(3) 75WF, 3% OSA modified corn starch As shown in Table 9, the starch containing spray solutions improved rainfastness resulting in reduced % Fresh Weight.

EXAMPLE 7

Several starch samples containing Atplus MBA 13/15 (C12–C15 monobranched ethoxylated alcohol) surfactant were prepared as powders, as in the above examples, and identified below in Table 10. Two of the samples, D and E, are made by a process where a porous drum dried or spray dried starch particle is made containing no load. Subsequently a non-aqueous liquid or molten load component is absorbed into the porous structures to give a stable loaded particulate. These powders containing the starch entrapped surfactant were tested for the effect on azoxystrobin fungicide activity against Septoria tritici fungus on winter wheat. In one sample, the azoxystrobin was applied as a control using 0.5 l/ha of a commercial formulation Quadris (Syngenta) which contained 250 g/l of azoxystrobin (no surfactant), sample C. Additional treatments were carried out applying 0.5 l/ha of the commercial formulation Quadris containing 250 g/l of azoxystrobin and 0.1% weight by volume (of the spray volume), of the starch entrapped surfactant (samples A, B and D–E) and another comparative sample containing the fungicide plus surfactant without starch (sample C-1). These samples were applied to winter wheat c v Riband by spraying at 200 l/ha. The % infection remaining was determined on the second (2) and third (3) leafs of the treated plants, 25 days after inoculation and are shown in Table 11.

TABLE 10

| Sample | Starch | Ratio starch/surfactant |
|---|---|---|
| A | 3% OSA modif. waxy maize | 50/50 |
| B | cationic crosslinked waxy maize | 50/50 |
| D | puffed, spray dried waxy maize | 50/50 |
| E | tapioca dextrin | 50/50 |

TABLE 11

Effect of Starch/Surfactant with Fungicide on Winter Wheat

| | % Infection | |
|---|---|---|
| Sample | Leaf 2 | Leaf 3 |
| C (fungicide alone) | 16.6 | 40.0 |
| C-1 (fungicide/surfactant) | 4.7 | 33.0 |
| A (fungicide/starch/surfactant) | 0 | 16.5 |
| B (fungicide/starch/surfactant) | 1.8 | 10.4 |

TABLE 11-continued

Effect of Starch/Surfactant with Fungicide on Winter Wheat

| | % Infection | |
|---|---|---|
| Sample | Leaf 2 | Leaf 3 |
| D (fungicide/starch surfactant) | 1.2 | 6.1 |
| E (fungicide/starch/surfactant) | 4.7 | 11.3 |

As shown by the results given in Table 11, the combination of starch and surfactant (samples A–E) increases the biological efficacy of the fungicide used alone (sample C) or the fungicide with surfactant (sample C-1).

EXAMPLE 8

Starch sample A containing a 50/50 by weight ratio of a puffed, spray dried waxy maize and Atlox MBA 13/15 (C12–C15 monobranched ethoxylated alcohol) and starch sample B containing a 50/50 by weight ratio of tapioca dextrin and Atlox MBA 13/15 (C12–C15 monobranched ethoxylated alcohol) were prepared. The starch samples were prepared in a similar manner to samples D and E of Example 7. The prepared starch powders (A and B) were tested for the effect on azoxystrobin fungicide activity against Septoria tritici fungus on winter wheat (vagabond). Additional treatments were carried out using comparative samples which contained the azoxystrobin fungicide (250 g/l) with Atlox MBA 13/15 alone (C-1), Amistar, a commercial formulation which contained azoxystrobin (250 g/l) plus an adjuvant (C-2), and Quadris, a commercial formulation which contained azoxystrobin (250 g/l) alone (C-3). Samples A, B, C-1 and C-3 were prepared to deliver 187.5 g of the azoxystrobin per hectare and 300 ml of the adjuvant when applied to the winter wheat (vagabond) with a spray volume of 300 l/ha. Sample C-2 was prepared to deliver 250 g/l of the azoxystrobin per hectare when applied to winter wheat (vagabond) with a spray volume of 300 l/ha; concentration of the built-in adjuvant is unknown. The % infection was determined on the treated plants 1, 2 and 3 weeks after treatment (WAT) and the results are shown in Table 12.

TABLE 12

Effect of Starch/Surfactant/Adjuvant with Fungicide on Winter Wheat

| | % Infection | | |
|---|---|---|---|
| Sample (1) | 1 WAT | 2 WAT | 3 WAT |
| A | 22.5 | 23.1 | 21.7 |
| B | 25 | 25 | 25 |
| C-1 | 20 | 25 | 35 |
| C-2 | 27.5 | 22.5 | 30 |
| C-3 | 32.5 | 30 | 35 |

(1) A—50/50 waxy maize/Atlox MBA 13/15 and azoxystrobin
B—50/50 tapioca dextrin/Atlox MBA 13/15 and azoxystrobin
C-1—Atlox MBA 13/15 and azoxystrobin
C-2—adjuvant and azoxystrobin
C-3—azoxystrobin The results in Table 12 show that the addition of the starch to surfactant/adjuvant (Samples A and B) extends the effectiveness of the fungicide in maintaining a lower % infection.

EXAMPLE 9

This example illustrates the production of a solid formulation containing high loading of two (2) dissimilar active materials.

A cooked octenyl succinic anhydride (OSA) waxy maize starch/corn syrup was blended with aqueous glyphosate-IPA solution and then 2,4-D-2-ethylhexyl (liquid oil) was added (formulations given in Table 13 below). The formulations were subjected to high shear mixing until the particle size stabilized (i.e. reduced particle size to low level) and an emulsion formed. Water was added to reduce the viscosity to a level acceptable for atomization. The solution was spray dried in a Mobile Minor spray dryer to get a solid powder product. The powder was collected and then redispersed by mixing with water (3 g powder/100 ml water) with gentle agitation. The dispersion was then checked for emulsion stability, compatibility and emulsion/oil droplet size with the results given in Table 14.

TABLE 13

Multiactive/Starch Formulations

| | Formulations (w/w %) | | | |
|---|---|---|---|---|
| Components | F1 | F2 | F3 | F4 |
| Glyphosate - IPA | 20 | 25 | 27.5 | 20 |
| 2,4-D-2-ethylhexyl | 20 | 25 | 27.5 | 20 |
| Waxy maize, OSA/corn syrup | 60 | 50 | 45 | |
| Waxy maize, OSA/corn syrup | | | | 60 |

TABLE 14

Multiactive/Starch Formulation Evaluations

| | Formulations | | | |
|---|---|---|---|---|
| | F1 | F2 | F3 | F4 |
| Feedstock-PSD(1) (40% solids) | 0.468 | 0.699 | 0.55 | 0.431 |
| Redispers. powder-PSD (3% w/v) | 0.852 | 0.411 | 0.488 | 0.414 |
| Emulsion stability (after 24 hrs)(2) water hardness | | | | |
| 50 ppm | TS | TS | TS | TS |
| 342 ppm | TS | TS | TS | TS |
| 1000 ppm | TS | TS | TS | TS |

(1)PSD—particle size distribution d(0.5) in micron
(2)TS—trace of sediment

The emulsion/solutions evaluated were functionally homogenous, showed no creaming, phasing or separation (after 4 hours) and minimal sedimentation (TS—trace of sediment after 24 hours). The particle size of the redispersed powders were comparable to the corresponding feedstock. Neither the glyphosate nor the 2,4-D-2-ethylhexyl separated in the redispersed powder/granule.

The above describes the preparation of a stable solid product which contains two (2) dissimilar active materials, i.e. the water soluble glyphosphate-IPA and the non-water soluble 2,4-D-2-ethylhexyl material. The stable powder exhibited good emulsion properties.

What is claimed is:
1. A stable, solid formulation which is water dispersible and compatible when dispersed in water and comprises:
   a.) a chemically modified starch,
   b.) a biologically active agricultural material, and
   c.) a surfactant and/or adjuvant, wherein from about 30 to 70% by weight is load and from about 30 to 70% by weight is starch.

2. The composition of claim 1 wherein the modified starch is a starch ester or starch ether.

3. The composition of claim 2 wherein the starch is a starch ester prepared from an organic acid anhydride having a hydrophobic hydrocarbon group of 2 to 22 carbon atoms.

4. The composition of claim 3 wherein the hydrocarbon group is selected from alkyl, alkenyl, aralkyl and aralkenyl groups.

5. The composition of claim 4 wherein the hydrocarbon group has 5 to 18 carbon atoms.

6. The composition of claim 2 wherein the starch is a starch ether prepared by modifying the starch with alkylene oxide having 2 to 6 carbon atoms.

7. The composition of claim 6 wherein the starch is modified with up to 25% by weight of alkylene oxide which has 2 to 4 carbon atoms.

8. The composition of claim 1 wherein the biologically active material is selected from the group consisting of herbicides, insecticide, and fungicides.

9. The composition of claim 8 wherein the surfactant is selected from the group consisting of alcohol alkoxylates having C8 to C18 alcohols, alkylamine alkoxylates having C8 to C18 alkylamines, sorbitol, sorbitan fatty acid esters having C8 to C18 fatty acid esters and their ethoxylated derivatives and chemically modified low molecular weight alkyl polysaccharides having C6 to C14 alkyl groups.

10. The composition of claim 9 wherein the modified starch is a starch ester or starch ether.

11. The composition of claim 10 wherein the starch is starch ester modified with an organic acid anhydride having a hydrocarbon group of 2 to 22 carbon atoms and is selected from alkyl, alkenyl, aralkyl or aralkenyl groups.

12. The composition of claim 11 wherein the hydrocarbon group has 5 to 18 carbon atoms.

13. The composition of claim 11 wherein the biologically active material is a glyphosate.

14. The composition of claim 13 wherein the surfactant is a C6–C14 alkyl polyglycoside.

15. The composition of claim 10 wherein the starch is a starch ether prepared by modifying the starch with alkylene oxide having 2 to 6 carbon atoms.

16. The composition of claim 1 wherein more than one of the chemically modified starch and/or more than one of the surfactant/adjuvants are used.

17. The composition of claim 16 wherein more than one of the biologically active materials are used.

18. The composition of claim 1 wherein more than one of the biologically active materials are used.

19. The composition of claim 18 wherein the modified starch is a starch ester or starch ether.

20. The composition of claim 19 wherein the starch is a starch ester prepared from an organic acid anhydride having a hydrophobic hydrocarbon group of 2 to 22 carbon atoms.

21. A stable, solid formulation which is water dispersible and compatible when dispersed and comprises:
   a.) a chemically modified starch, and
   b.) a biologically active agricultural material, wherein from about 30 to 70% by weight is load and from about 30 to 70% by weight is starch.

22. The composition of claim 21 wherein more than one of the biologically active materials are used.

23. The composition of claim 22 wherein the modified starch is a starch ester on starch ether.

24. The composition of claim 21 wherein the biologically active material is selected from the group consisting of herbicides, insecticides and fungicides.

25. The composition of claim 24 wherein the modified starch is a starch ester or starch ether.

26. The composition of claim 25 wherein the biologically active agricultural material is a glyphosate.

27. A stable, solid formulation which is water dispersible and compatible when dispersed and consists essentially of:
   a.) a chemically modified starch and
   b.) a surfactant or non-oil adjuvant, wherein from 18 to 85 by weight is load and from about 18 to 85% by weight starch.

28. The composition of claim 27 wherein the modified starch is starch ester or starch ether.

29. The composition of claim 28 wherein the starch is a starch ester modified with an organic acid anhydride having a hydrophobic hydrocarbon group of 2 to 22 carbon atoms.

30. The composition of claim 28 wherein the surfactant is a C6–C14 alkyl polyglycoside.

31. The composition of claim 28 wherein from about 30 to 70% by weight, dry basis, of the load which comprises the total amount of the surfactant, adjuvant and other ingredients and from about 30 to 70% by weight, dry basis, of the starch are used.

32. The composition of claim 27 wherein more than one of the chemically modified starch and/or surfactant or adjuvants are used.

33. The composition of claim 32 wherein the modified starch is a starch ester or starch ether.

34. An aqueous dispersion containing a biologically active agricultural material and having increased biological efficacy comprising:
   a.) a chemically modified starch,
   b.) a biologically active agricultural material, and optionally
   c.) a surfactant/ and/or adjuvant.

35. The composition of claim 34 wherein the modified starch is a starch ester or starch ether.

36. The composition of claim 35 wherein the biologically active material is selected from the group consisting of herbicides, insecticides and fungicides.

37. The composition of claim 35 wherein the biologically active material is a glyphosate or strobilurin.

38. The composition of claim 35 wherein the biologically active material is glyphosate-isopropyl amine or azoxystrobin.

39. The composition of claim 37 wherein a non-ionic surfactant is used.

40. The composition of claim 39 wherein the surfactant is an ethoxylated C8 to C18 alcohol.

41. A method of applying a biologically active agricultural material to agricultural crops, vegetation, weeds, plants, insects, pests and soil comprising applying an aqueous dispersion of:
   a.) a chemically modified starch,
   b.) a biologically active agricultural material, and optionally
   c.) a surfactant and/or adjuvant, characterized in that an increased effect of biological efficacy of the active material is provided.

42. The method of claim 41 wherein the modified starch is a starch ester or starch ether.

43. The method of claim 42 wherein the biologically active material is selected from the group consisting of herbicides, insecticides and fungicides.

44. The method of claim 42 wherein the biologically active material is a glyphosate or strobilurin.

45. The method of claim 42 wherein the biologically active material is glyphosate-isopropyl amine or azoxystrobin.

46. The method of claim 44 wherein a non-ionic surfactant is used.

47. The method of claim 46 wherein the surfactant is an ethoxylated C8 to C18 alcohol.

48. The method of claim 46 wherein the surfactant is a C6 to C14 alkyl polyglycoside.

* * * * *